(12) United States Patent
Wada

(10) Patent No.: US 10,058,458 B2
(45) Date of Patent: Aug. 28, 2018

(54) DEVICE FOR MANUFACTURING ELASTIC LAMINATE AND METHOD FOR MANUFACTURING ELASTIC LAMINATE

(71) Applicant: ZUIKO CORPORATION, Osaka (JP)

(72) Inventor: Takao Wada, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 176 days.

(21) Appl. No.: 15/027,377

(22) PCT Filed: Sep. 25, 2014

(86) PCT No.: PCT/JP2014/075504
§ 371 (c)(1),
(2) Date: Apr. 5, 2016

(87) PCT Pub. No.: WO2015/053088
PCT Pub. Date: Apr. 16, 2015

(65) Prior Publication Data
US 2016/0242967 A1    Aug. 25, 2016

(30) Foreign Application Priority Data

Oct. 10, 2013  (JP) .................................. 2013-213065
Oct. 10, 2013  (JP) .................................. 2013-213066
Oct. 10, 2013  (JP) .................................. 2013-213067

(51) Int. Cl.
*A61F 13/15* (2006.01)
*B32B 37/14* (2006.01)
*B32B 37/00* (2006.01)

(52) U.S. Cl.
CPC .... *A61F 13/15593* (2013.01); *B32B 37/0053* (2013.01); *B32B 37/144* (2013.01);
(Continued)

(58) Field of Classification Search
CPC .......... A61F 13/15593; A61F 13/15601; A61F 13/15609; B32B 2555/02
See application file for complete search history.

(56) References Cited

U.S. PATENT DOCUMENTS

2003/0010423 A1  1/2003  Nakakado et al.
2004/0081794 A1  4/2004  Titone
(Continued)

FOREIGN PATENT DOCUMENTS

JP  9-70412  3/1997
JP  2001-178769  7/2001
(Continued)

OTHER PUBLICATIONS

International Search Report.
European Search Report dated Nov. 30, 2016.

*Primary Examiner* — Carson Gross
(74) *Attorney, Agent, or Firm* — Gerald E. Hespos; Michael J. Porco; Matthew T. Hespos

(57) ABSTRACT

It is aimed to provide a device for manufacturing an elastic laminate which device can stably position an elastic member with respect to both sheets. A drive mechanism includes a timing belt having a guide plate fixed thereto, a plurality of timing pulleys configured such that the timing belt is provided thereon along an annular path including a travel path, a motor configured to drive the timing pulleys to be successively rotated in forward and reverse directions to reciprocate the guide plate along the travel path, and a slider and a rail configured to permit a movement of the guide plate relative to both nip rolls along the travel path and regulate a movement of the guide plate relative to the both nip rolls in a direction orthogonal to the travel path.

19 Claims, 8 Drawing Sheets

(52) U.S. Cl.
  CPC ... *A61F 13/15601* (2013.01); *A61F 13/15609* (2013.01); *B32B 2555/00* (2013.01)

(56) References Cited

U.S. PATENT DOCUMENTS

| | | | |
|---|---|---|---|
| 2004/0123954 A1 * | 7/2004 | Yoneoka | A61F 13/15593 |
| | | | 156/494 |
| 2010/0078119 A1 | 4/2010 | Yamamoto | |
| 2010/0078120 A1 | 4/2010 | Otsubo | |

FOREIGN PATENT DOCUMENTS

| | | | | |
|---|---|---|---|---|
| JP | 2001178769 A | * | 7/2001 | ....... A61F 13/15601 |
| JP | 2003-38565 | | 2/2003 | |
| JP | 2004-155586 | | 6/2004 | |
| JP | 2006-141642 | | 6/2006 | |

\* cited by examiner

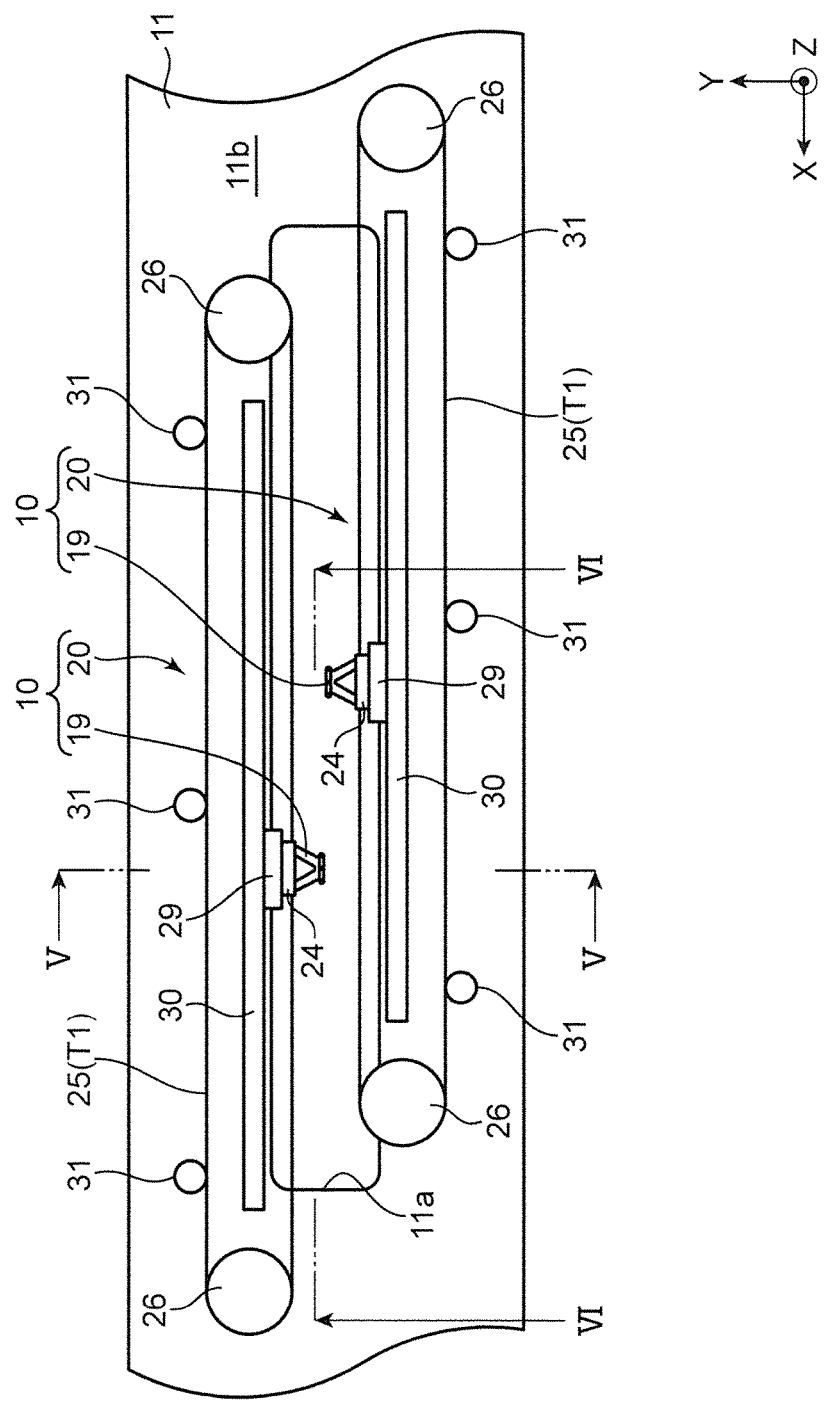

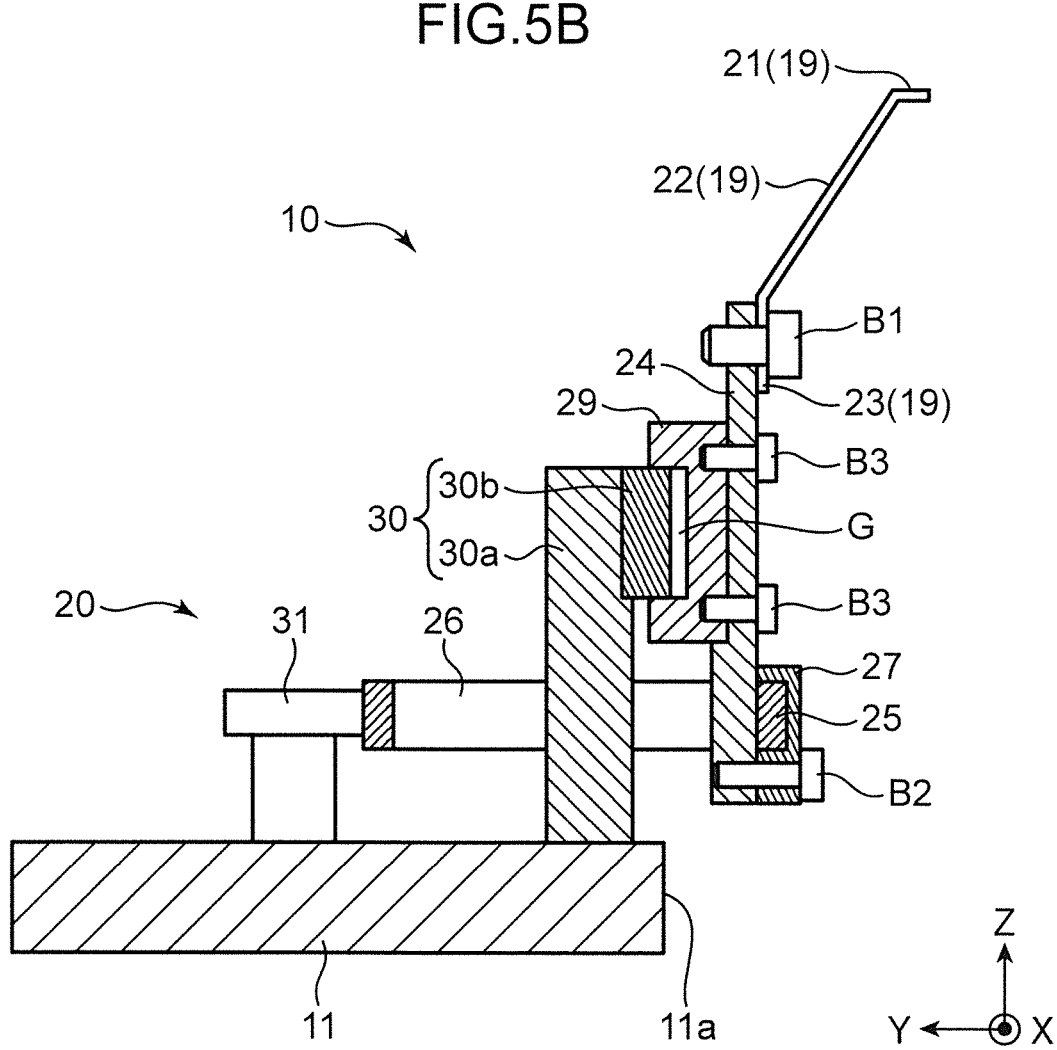

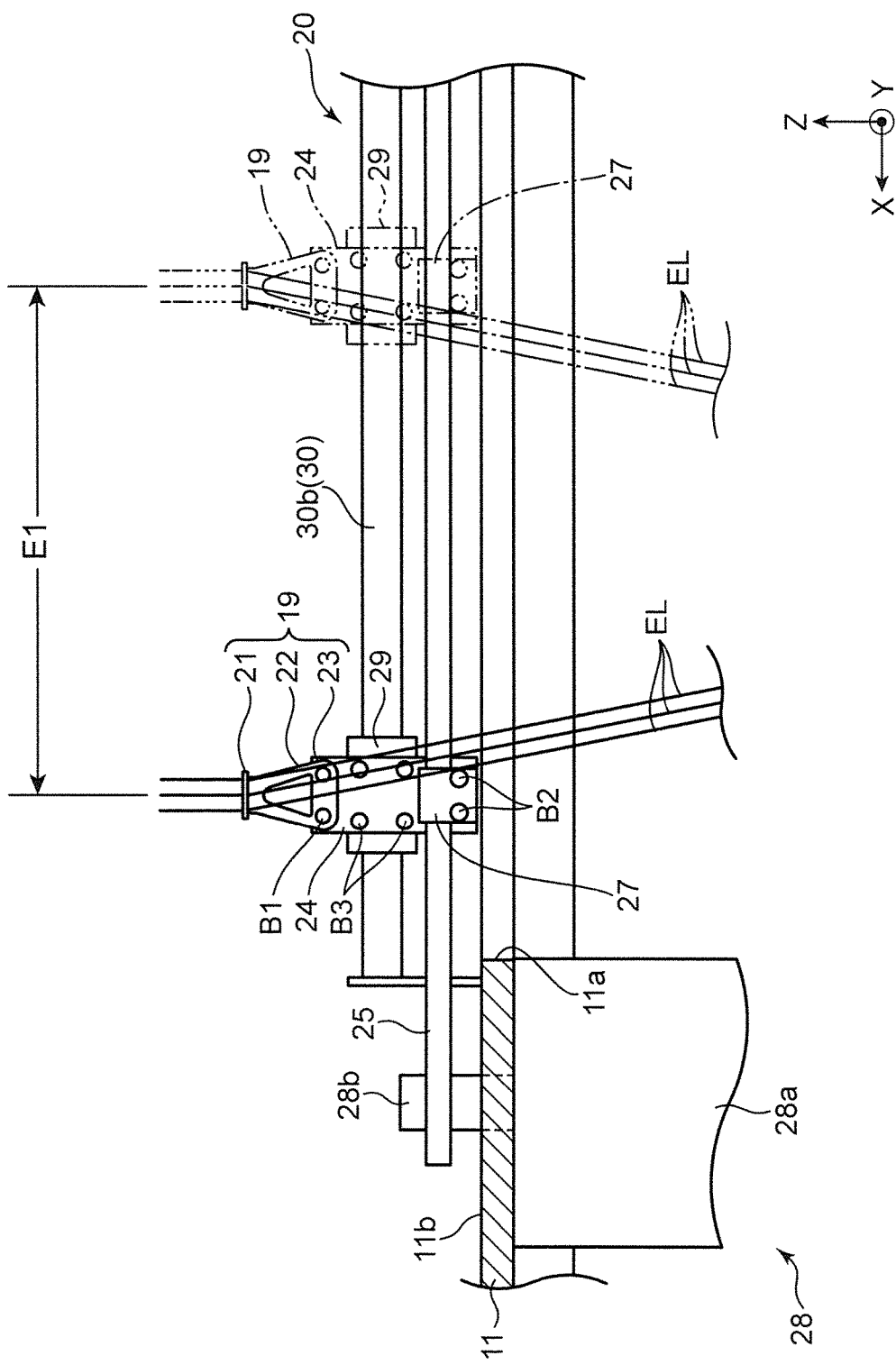

DEVICE FOR MANUFACTURING ELASTIC LAMINATE AND METHOD FOR MANUFACTURING ELASTIC LAMINATE

TECHNICAL FIELD

The present invention relates to a device and a method for manufacturing an elastic laminate in which an elastic member is sandwiched between a pair of sheets.

BACKGROUND ART

Conventionally, a device for manufacturing a disposable wearable article described in Japanese Unexamined Patent Publication No. 2003-38565 is, for example, known as a device for manufacturing an elastic laminate.

The manufacturing device described in Japanese Unexamined Patent Publication No. 2003-38565 is provided with a pair of nip rolls configured to sandwich a pair of sheets with an elastic member interposed between the both sheets conveyed in longitudinal directions, a guide member provided upstream of the both nip rolls in the conveying directions of the both sheets and configured to guide the elastic member to between the both sheets while feeding the elastic member in a longitudinal direction thereof, and a drive mechanism configured to drive the guide member to change the position of the elastic member with respect to the both sheets.

The pair of nip rolls are so arranged that axes of both nip rolls are parallel.

The drive mechanism drives the guide member so that the guide member reciprocates along a travel path along the axial direction of the both nip rolls.

Specifically, the drive mechanism includes a belt having the guide member fixed thereto, a pair of pulleys configured such that the belt is provided thereon along an annular path including the travel path and a motor configured to drive the pulleys to be successively rotated in forward and reverse directions to reciprocate the guide member along the travel path.

The guide member is moved by this drive mechanism, whereby the elastic member can be sandwiched between the both sheets while changing the position of the elastic member along the axial direction of the both nip rolls.

Further, since the motor is provided to reciprocate the guide member by rotating and driving the pulleys successively in the forward and reverse directions, the configuration of the manufacturing device can be simplified as compared to the case of providing a mechanism (cam, etc.) for reciprocating the guide member.

However, since the guide member is fixed only to an intermediate part of the belt provided across the pair of pulleys in the drive mechanism described in Japanese Unexamined Patent Publication No. 2003-38565, the guide member may move in a direction orthogonal to the travel path when the belt moves.

If the guide member moves in the direction orthogonal to the travel path, the position of the guide member with respect to the both nip rolls changes, thereby causing a problem that the position of the elastic member between the both sheets becomes unstable.

SUMMARY OF INVENTION

The present invention aims to provide a device for manufacturing an elastic laminate which device is capable of stably positioning an elastic member with respect to both sheets.

To solve the above problem, the present invention provides a device for manufacturing an elastic laminate in which an elastic member is sandwiched between a pair of sheets, the device including a pair of nip rolls configured to sandwich the pair of sheets with the elastic member interposed between the both sheets conveyed in longitudinal directions of the sheets and arranged such that axes of the pair of nip rolls are parallel, a guide member provided upstream of the both nip rolls in the conveying directions of the both sheets and configured to guide the elastic member to between the both sheets while feeding the elastic member in a longitudinal direction of the elastic member, and a drive mechanism configured to drive the guide member such that the guide member reciprocates along a travel path along a direction of the axes of the both nip rolls, the drive mechanism including a belt having the guide member fixed thereto, a plurality of pulleys configured such that the belt is provided thereon along an annular path including the travel path, a motor configured to drive the pulleys to be successively rotated in forward and reverse directions to reciprocate the guide member along the travel path and a regulating mechanism configured to permit a movement of the guide member relative to the both nip rolls along the travel path and regulate a movement of the guide member relative to the both nip rolls in a direction orthogonal to the travel path.

Further, the present invention provides a method for manufacturing an elastic laminate using the above manufacturing device, the method including a conveying step of conveying the pair of sheets in longitudinal directions of the pair of sheets such that the sheets are guided to between the pair of nip rolls, a guiding step of guiding the elastic member to between the both sheets while feeding the elastic member in a longitudinal direction of the elastic member using the guide member such that the elastic member is sandwiched between the both sheets by the pair of nip rolls, and a driving step of driving the guide member using the drive mechanism such that the guide member reciprocates along a travel path along a direction of axes of the both nip rolls, in the driving step, a movement of the guide member relative to the both nip rolls along the travel path is permitted and a movement of the guide member relative to the both nip rolls in a direction orthogonal to the travel path is regulated using the regulating mechanism.

According to the present invention, it is possible to stably position an elastic member with respect to both sheets.

BRIEF DESCRIPTION OF DRAWINGS

FIG. 4 is a plan view enlargedly showing a part of FIG. 3.

FIG. 5B is a sectional view enlargedly showing a part of FIG. 5A in a state where no tension is applied to a belt.

FIG. 6 is a sectional view along line VI-VI of FIG. 4.

DESCRIPTION OF EMBODIMENT

Hereinafter, an embodiment of the present invention is described with reference to the accompanying drawings. Note that the following embodiment is a specific example of the present invention and not of the nature to limit the technical scope of the present invention.

First, an elastic laminate L manufactured by a manufacturing device according to the embodiment of the present invention is described with reference to FIG. 1.

The elastic laminate L is such that elastic members EL are sandwiched between a pair of sheets S1, S2.

In the case of manufacturing this elastic laminate L, adhesive is applied to at least one of the sheets S1, S2 and the elastic members EL.

Subsequently, the both sheets S1, S2 are respectively conveyed in longitudinal directions thereof to meet at a junction set in advance as indicated by arrows Y1.

Together with the conveyance of these sheets S1, S2, the elastic members EL are guided to a position between the both sheets S1, S2 at the junction while being fed in longitudinal directions thereof.

At the junction, the both sheets S1, S2 are sandwiched by a pair of nip rolls 5 (see FIG. 2) to be described later. In this way, the both sheets S1, S2 and the elastic members EL are bonded to manufacture the elastic laminate L.

Note that the elastic members EL are guided to between the both sheets S1, S2 while reciprocating in directions orthogonal to the longitudinal directions of the both sheets S1, S2 as indicated by arrows Y2. Thus, the elastic members EL are sandwiched between the both sheets S1, S2 while changing the position thereof in the directions orthogonal to the longitudinal directions of the both sheets S1, S2.

Figure 1:
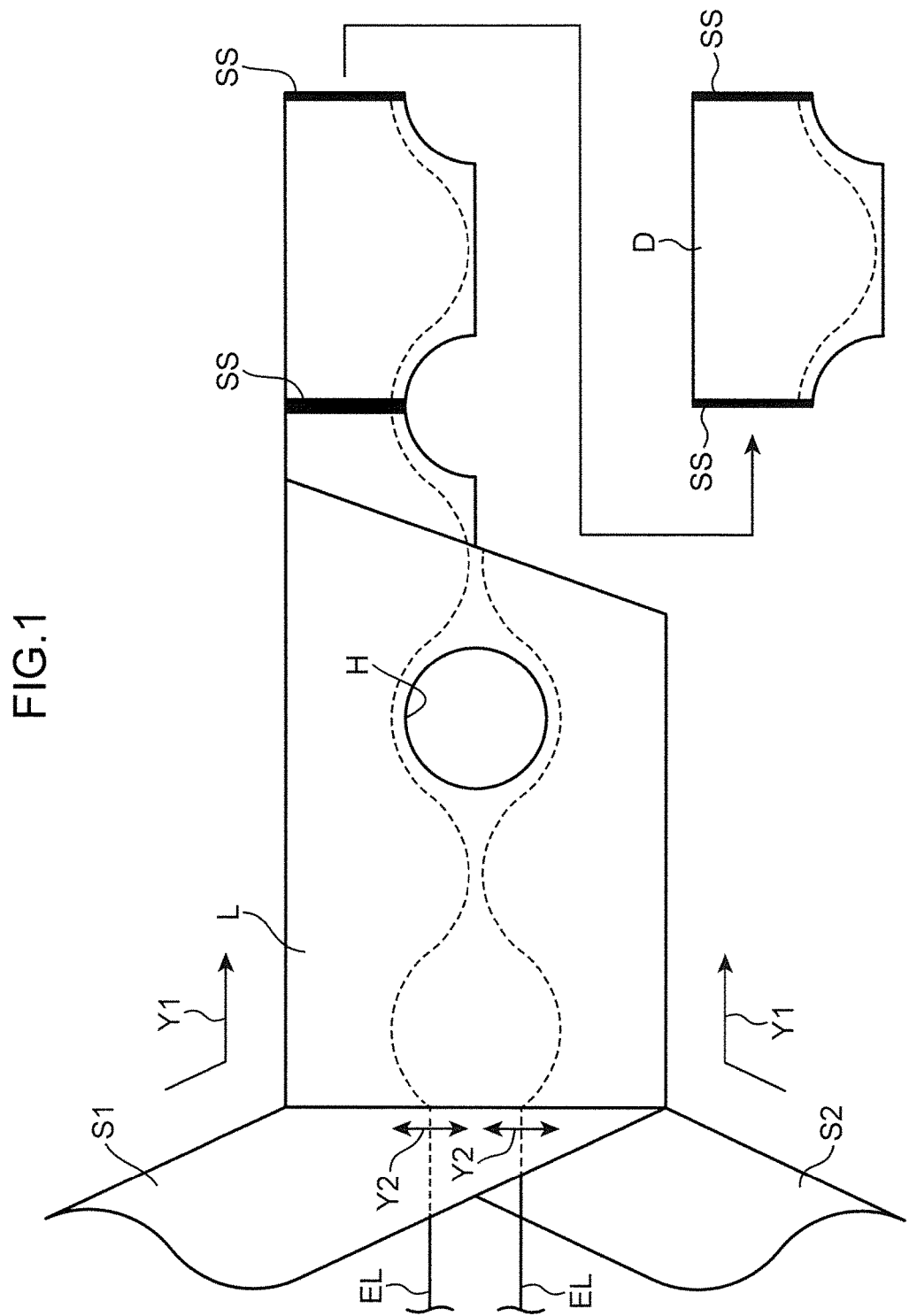
FIG. 1 is a schematic diagram showing a manufacturing process of an elastic laminate manufactured by a manufacturing device according to an embodiment of the present invention.

FIG. 1 shows an example in which the both elastic members EL are so provided between the both sheets S1, S2 that convex parts and concave parts of sign curves defined by the both elastic members EL are in the same phase with each other.

The elastic laminate L is, for example, used for disposable diapers D.

Specifically, in FIG. 1, a leg hole H is formed at a position between the convex part of the sine curve defined by one elastic member EL and the concave part of the sine curve defined by the other elastic member EL (position where the both elastic members EL are most distant from each other), and the elastic laminate L is doubled in a direction orthogonal to the conveying direction Y1 thereof.

Subsequently, parts of the doubled elastic laminate L near the top of the leg hole H are welded in the direction orthogonal to the conveying direction Y1 to form side seal parts SS, these side seal parts SS are cut to divide the elastic laminate L for the disposable diapers D.

Note that it is also possible to join an absorber at a position between two adjacent leg holes H on the elastic laminate L before being doubled.

The manufacturing device 1 for the elastic laminate L is described with reference to FIG. 2 below.

The manufacturing device 1 is provided with a sandwiching unit 2 including a pair of nip rolls 5 for sandwiching the both sheets S1, S2 with the elastic members EL interposed between the both sheets S1, S2 conveyed in the longitudinal directions, a guiding unit 3 provided upstream of the both nip rolls 5 in the conveying directions of the both sheets S1, S2 and configured to guide the elastic members EL to between the both sheets S1, S2, and a supporting unit 4 configured to support the sandwiching unit 2 and the guiding unit 3.

The both nip rolls 5 are so arranged that axes 5a thereof are parallel to each other. Note that, in the following description, an extending direction of the axes 5a of the both nip rolls 5 is referred to as an X direction, an arrangement direction of the both nip rolls 5 as a Y direction and a direction orthogonal to the X and Y directions as a Z direction.

The sandwiching unit 2 includes a sandwiching main body 7 for supporting the both nip rolls 5 rotatably about the axes 5a, brackets 8 provided at opposite ends of the sandwiching main body 7 in the Y direction and a motor 9 for driving the both nip rolls 5 to be rotated such that the both sheets S1, S2 are conveyed in the conveying direction Y1 (see FIG. 1).

Figure 2:
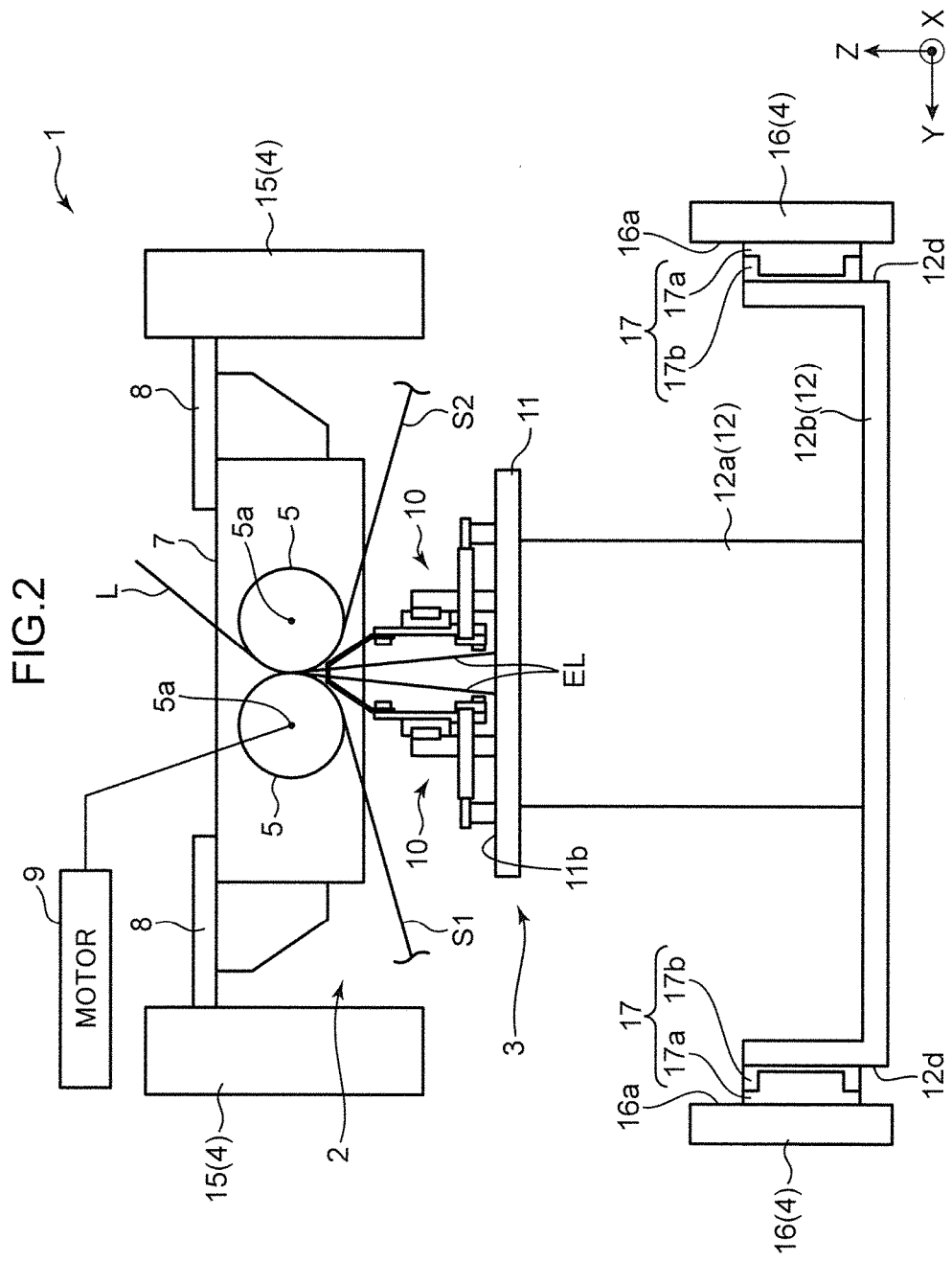
FIG. 2 is a front view showing the overall configuration of the manufacturing device according to the embodiment of the present invention.

Note that although the motor 9 and the sandwiching main body 7 are shown to be separated in FIG. 2 for the sake of convenience, the motor 9 is held on the sandwiching main body 7.

The guiding unit 3 includes a pair of reciprocation guide mechanisms 10 arranged side by side in the Y direction, a base plate 11 having the both reciprocation guide mechanisms 10 attached thereto and a placing table 12 having the base plate 11 placed thereon.

The placing table 12 includes a pedestal 12a for supporting the base plate 11, a slide base 12b, the pedestal 12a standing on the slide base 12b, and a pair of lock bars (see FIG. 3) 12c extending in the X direction from an end surface of the slide base 12b in the X direction.

Note that a specific configuration of the reciprocation guide mechanisms 10 is described in detail later.

The configuration of the supporting unit 4 is described with reference to FIGS. 2 and 3. Note that FIG. 3 is a plan view of the manufacturing device 1 with the sandwiching unit 2 in FIG. 2 omitted.

The supporting unit 4 supports the sandwiching unit 2 and the guiding unit 3 such that the sandwiching unit 2 and the guiding unit 3 are relatively displaceable along the X direction.

Figure 3:
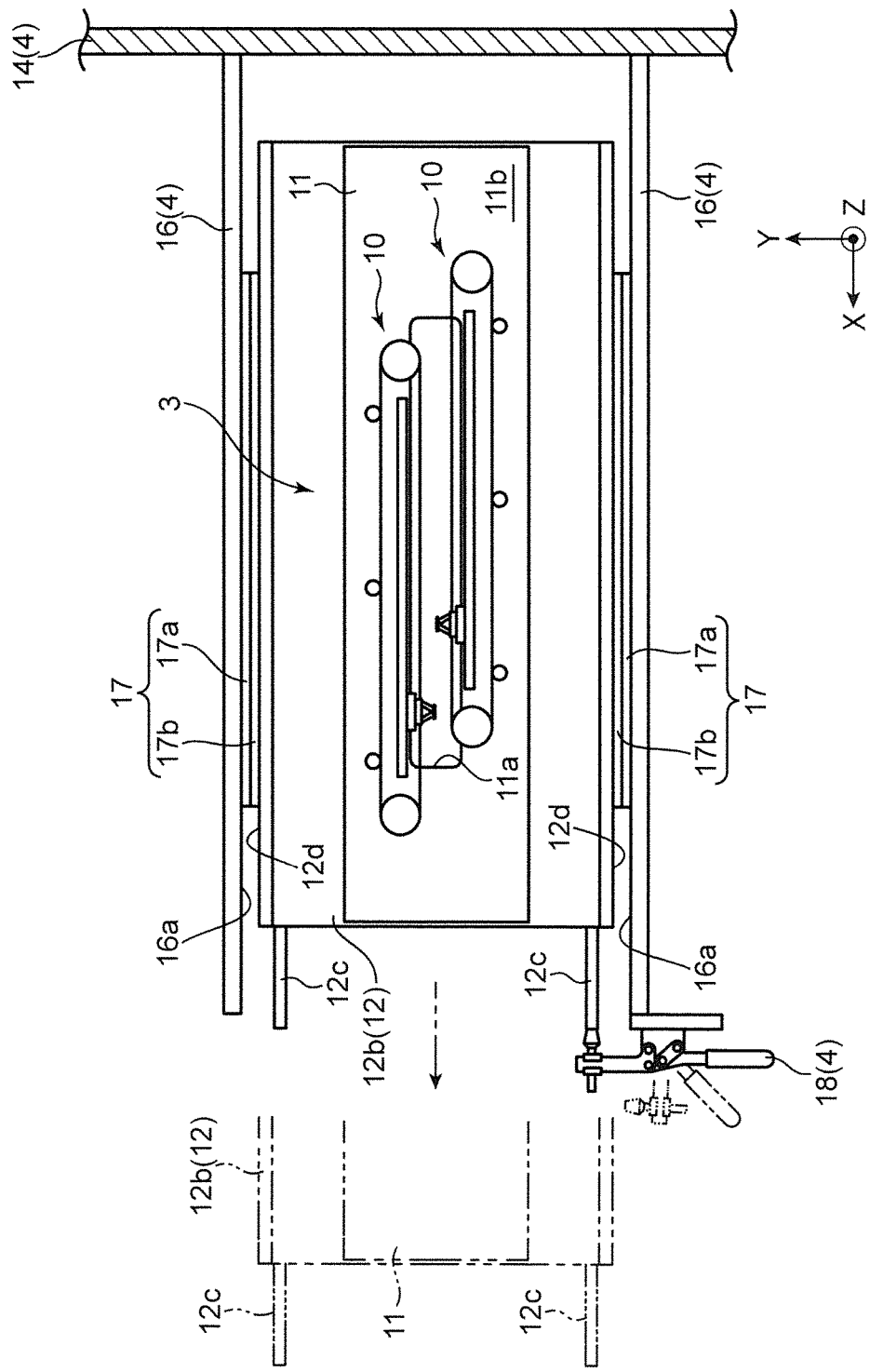
FIG. 3 is a plan view showing the manufacturing device shown in FIG. 2 with a sandwiching unit omitted.

Specifically, the supporting unit 4 includes a main frame 14 provided on one side in the X direction with respect to the sandwiching unit 2 and the guiding unit 3, a pair of sandwiching unit holding beams (sandwiching unit holding mechanism) 15 extending in the X direction from the main frame 14 and configured to hold the sandwiching unit 2, a pair of guiding unit holding beams (guiding unit holding mechanism) 16 extending in the X direction from the main frame 14 and configured to hold the guiding unit 3, a pair of linear guides (guiding unit holding mechanism) 17 provided between the both guiding unit holding beams 16 and the guiding unit 3 and lock members (guiding unit holding mechanism) 18 respectively provided on tip parts of the both guiding unit holding beams 16 (one lock member 18 is not shown in FIG. 3).

The both sandwiching unit holding beams 15 are arranged at opposite sides of the sandwiching unit 2 in the Y direction and respectively fixed to the brackets 8 of the sandwiching unit 2.

The both guiding unit holding beams 16 are arranged outwardly of the both sandwiching unit holding beams 15 in the Y direction. That is, the both guiding unit holding beams 16 are spaced apart in the Y direction by a distance longer than a width of the sandwiching unit 2 in the Y direction.

Further, the both guiding unit holding beams 16 hold the guiding unit 3 via the both linear guides 17 such that the guiding unit 3 is movable in the X direction between the guiding unit holding beams 16.

Specifically, the both linear guides 17 include support-side guides 17a respectively fixed to inner side surfaces 16a of the both guiding unit holding beams 16 and guide-side guides 17b respectively fixed to both outer side surfaces 12d of the slide bases 12b of the guiding unit 3.

The support-side guides 17a and the guide-side guides 17b are relatively displaceable in the X direction and engaged with each other in a state where they cannot be relatively displaced in directions orthogonal to the X direction.

The lock members 18 are switchable between a regulating state for regulating a movement of the guiding unit 3 relative to the both guiding unit holding beam 16 (state shown by solid line in FIG. 3) and a permitting state for permitting a movement of the guiding unit 3 relative to the both guiding unit holding beams 16 (state shown by chain double-dashed line in FIG. 3).

Specifically, the lock members 18 are configured by toggle levers which press the lock bars 12c of the guiding unit 3 toward the main frame 14 side in the regulating state and, on the other hand, which release the pressing in the permitting state.

By switching the lock members 18 to the permitting state, the guiding unit 3 can be arranged at a position different from the sandwiching unit 2 in the X direction as shown by chain double-dashed line in FIG. 3. Thus, maintenance for the sandwiching unit 2 and/or the guiding unit 3 can be performed in a state where the guiding unit 3 is avoided from the sandwiching unit 2.

Further, since the sandwiching unit 2 and the guiding unit 3 are supported on one side in the X direction by the main frame 14, a space at a side opposite to the main frame 14 in the manufacturing device 1 can be utilized as a space for pulling out the guiding unit 3.

With the guiding unit 3 pulled out, the space on the side opposite to the main frame 14 in the manufacturing device 1 can be utilized as a space for the maintenance of the guiding unit 3.

Furthermore, since the sandwiching unit 2 is accessible through a space between the both guiding unit holding beams 16 with the guiding unit 3 pulled out, the operability of maintenance not only for the guiding unit 3, but also for the sandwiching unit 2 is improved.

The specific configuration of the pair of reciprocation guide mechanisms 10 of the guiding unit 3 is described below with reference to FIGS. 4 to 6.

Note that the both reciprocation guide mechanisms 10 are arranged at positions different in the X direction, but symmetrically configured with respect to an X-Z plane. Thus, only the configuration of the reciprocation guide mechanism 10 provided on the side of the left nip roll 5 shown in FIG. 5A with respect to a plane (X-Z plane) including a tangent to the outer circumferential surfaces of the both nip rolls 5 at a sandwiching position of the both sheets S1, S2 between the circumferential surfaces of the both nip rolls.

The reciprocation guide mechanism 10 includes a guide plate (guide member) 19 for guiding the elastic members EL to the both sheets S1, S2 while feeding the elastic members EL in the longitudinal direction thereof and a drive mechanism 20 for driving the guide plate 19 movably in the X direction.

Figure 7:
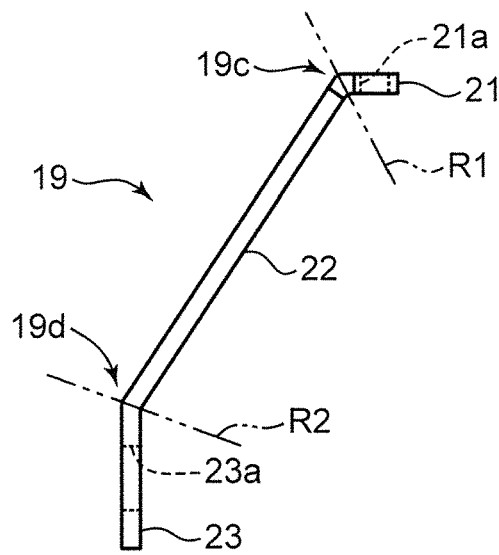
FIG. 7 is a front view enlargedly showing a guide plate of FIG. 5A.
Figure 8:
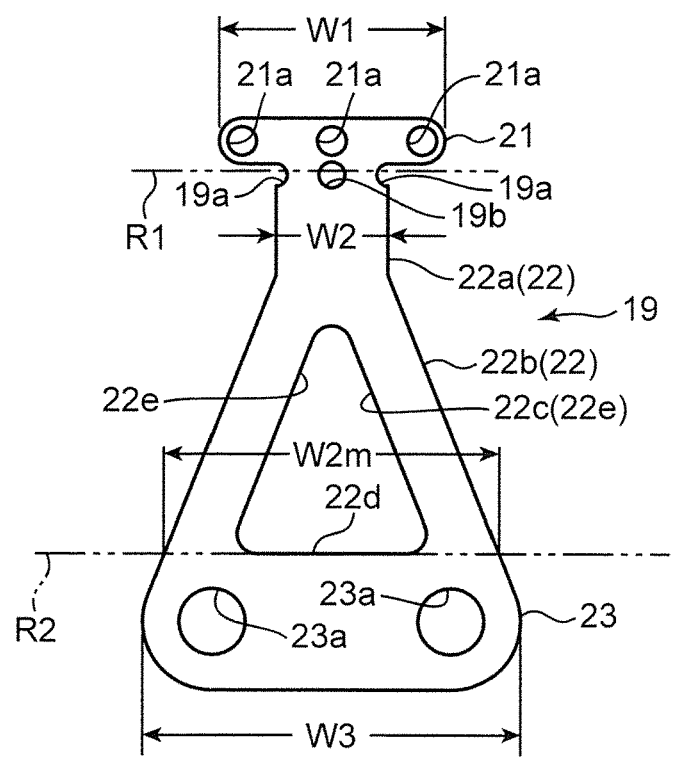
FIG. 8 is a plan view showing a developed state of the guide plate of FIG. 7.

The guide plate 19 is described below with reference to FIGS. 3, 7 and 8. Note that FIG. 8 is a plan view showing a developed state of bent portions of the guide plate 19.

The guide plate 19 is a metal plate (stainless steel plate) including a holding portion 21 for holding the elastic members EL feedably in the longitudinal direction thereof and a main body portion extending in a direction to avoid the left nip roll 5 from an end part of the holding portion 21 close to the left nip roll 5 (bent with respect to the holding portion 21) and attached to the drive mechanism 20. The main body portion includes a lead-out portion 22 extending from the holding portion 21 to an outer position outwardly of a part sandwiched between the outer circumferential surfaces of the both nip rolls 5 and an attaching portion 23 bent with respect to the lead-out portion 22 at the outer position and attached to the drive mechanism 20.

The holding portion 21 is arranged in a direction orthogonal to the tangent to the outer circumferential surfaces of the both nip rolls 5 at the sandwiching position of the both sheets S1, S2 between the outer circumferential surfaces of the both nip rolls 5.

Further, the holding portion 21 is formed with three insertion holes 21a penetrating through the holding portion 21 in a thickness direction (Z direction) and arranged side by side in the X direction (width direction of the holding portion 21). The elastic members EL are respectively inserted through these insertion holes 21a (see FIG. 6). This enables the holding portion 21 to hold the elastic members EL in a state where each elastic member EL is feedable in the longitudinal direction thereof while the guide plate 19 is moved in the X direction. Although the holding portion 21 according to this embodiment simultaneously guides the three elastic members EL, the number of the elastic members EL guided by the holding portion 21 is not limited.

The lead-out portion 22 extends from the holding portion 21 to the outer position outwardly of the part sandwiched between the outer circumferential surfaces of the both nip rolls 5. Further, the lead-out portion 22 includes a constant width portion 22a extending from the holding portion 21 while having a constant width W2 smaller than a width W1 of the holding portion 21 and a wide portion 22b gradually widened from the constant width portion 22a toward the attaching portion 23 to have a width W2m larger than the width W2. Here, the width W2m is larger than the width W1 of the holding portion 21.

The attaching portion 23 has a maximum width W3 larger than the width W2m.

The guide plate 19 is formed with a hold-side bent portion 19c bent along a folding line R1 between the holding portion 21 and the lead-out portion 22 and a attach-side bent portion 19d bent along a folding line R2 between the lead-out portion 22 and the attaching portion 23.

The hold-side bent portion 19c is formed with a pair of cuts (hold-side hollow portion) 19a formed by recessing opposite side surfaces of the guide plate 19 and a hold-side through hole (hold-side hollow portion) penetrating through the guide plate 19 in a thickness direction thereof between opposite side surfaces of the guide plate 19. By these cuts 19a and hold-side through hole 19b, a cross-sectional area of the hold-side bent portion 19c is made smaller than those of parts of the holding portion 21 and the lead-out portion 22 adjacent to the hold-side bent portion 19c.

The wide portion 22b is formed with a triangular through hole (attach-side hollow portion) 22c penetrating through the wide portion 22b in a thickness direction thereof. The triangular through hole 22c has a pair of oblique sides 22e parallel to opposite side surfaces of the wide portion 22b and a bottom side 22d coupling the both oblique sides 22e and constituting an end surface of the attaching portion 23. By this triangular through hole 22c, a cross-sectional area of the attach-side bent portion 19*d* is made smaller than that of a part of the attaching portion 23 adjacent to the attach-side bent portion 19*d*.

As described above, in the guide plate 19, the cross-sectional area of the hold-side bent portion 19*c* is made smaller than those of the parts adjacent to the hold-side bent portion 19*c* by the cuts 19*a* and the hold-side through hole (hold-side hollow portion) 19*b*, whereby the guide plate 19 can be bent at a position closer to a tip side. Thus, the small holding portion 21 corresponding to the positions of the cuts 19*a* and the hold-side through hole 19*b* can be realized.

Accordingly, the positions of the elastic members EL held by the holding portion 21 can be brought closer to the sandwiching position of the both nip rolls 5, whereby the positioning accuracy of the elastic members EL with respect to the both sheets S1, S2 can be improved.

In addition, since the cross-sectional area of the hold-side bent portion 19*c* is smaller than those of the parts adjacent to the hold-side bent portion 19*c*, the hold-side bent portion 19*c* is more easily elastically deformed as compared to the case where the hold-side bent portion 19*c* is not provided.

Thus, when the holding portion 21 receives a large force from the elastic members EL, the fracture of the elastic members EL can be suppressed by reducing sliding resistance against the elastic members EL by the elasticity of the hold-side bent portion 19*c*.

Moreover, since the weight of the guide plate 19 can be reduced by forming the cuts 19*a* and the hold-side through hole 19*b* penetrating through the guide plate 19, rigidity and power required for the drive mechanism 20 to be described later can be reduced.

Further, since the three elastic members EL arranged side by side in the X direction can be simultaneously guided to between the both sheets S1, S2 in the guide plate 19, it is possible to form the elastic laminate L in which the three elastic members EL are sandwiched in parallel to each other.

Here, if the width W1 of the holding portion 21 is simply set large to form a plurality of insertion holes 21*a* in the X direction on the holding portion 21, the hold-side bent portion 19*c* is difficult to elastically deform.

However, as described above, the cross-sectional area of the hold-side bent portion 19*c* is made smaller than those of the parts of the holding portion 21 adjacent to the hold-side bent portion 19*c* by the cuts 19*a* and the hold-side through hole 19*b*. Thus, the guiding of the plurality of the elastic members EL and easy elastic deformation of the hold-side bent portion 19*c* can be accomplished.

Further, since the maximum width W3 of the attaching portion 23 is larger than the maximum width W2*m* of the lead-out portion 22, the guide plate 19 (attaching portion 23) can be reliably attached to the drive mechanism 20 to be described later utilizing a wide area of the attaching portion 23.

Here, if the maximum width W3 of the attaching portion 23 is simply made larger than the maximum width W2*m* of the lead-out portion 22 to ensure the wide area of the attaching portion 23, the attach-side bent portion 19*d* is difficult to elastically deform.

However, in the above embodiment, the cross-sectional area of the attach-side bent portion 19*d* is made smaller than that of the part of the attaching portion 23 adjacent to the attach-side bent portion 19*d* by the triangular through hole 22*c*. Thus, reliable mounting of the attaching portion 23 and the drive mechanism 20 and easy elastic deformation of the attach-side bent portion 19*d* can be accomplished.

Accordingly, the fracture of the elastic members EL can be suppressed by reducing the sliding resistance of the elastic members EL also by the elasticity of the attach-side bent portion 19*d* according to the force received from the elastic members EL by the holding portion 21.

In addition, a further weight reduction of the guide plate 19 can be realized by the triangular through hole 22*c* penetrating through the guide plate 19.

Further, a weight reduction can be realized by suppressing an increase in the cross-sectional area of the wide portion 22*b* by the triangular through hole 22*c* while gradually increasing the width of the wide portion 22*b* toward the attaching portion 23.

Since the bottom side 22*d* of the triangular through hole 22*c* constitutes the end surface of the attaching portion 23, a sufficient area of the attaching portion 23 can be ensured.

The drive mechanism 20 is described below with reference to FIGS. 4 to 6.

The drive mechanism 20 drives the guide plate 19 such that the guide plate 19 reciprocates along a travel path E1 (see FIG. 6) along the X direction (direction of the axes of the both nip rolls 5).

Specifically, the drive mechanism 20 includes a attached member 24 to which the guide plate 19 is attached, a timing belt 25 attached to the attached member 24, a pair of timing pulleys 26 configured such that the timing belt 25 is provided thereon along an annular path T1 (see FIG. 4) including the travel path E1 of the guide plate 19, a motor 28 configured to drive the timing pulleys 26 to be successively rotated in both forward and reverse directions such that the guide plate 19 reciprocates along the travel path E1 and a regulating mechanism (slider 29 and rail 30) configured to permit a movement of the guide plate 19 relative to the both nip rolls 5 along the travel path E1 and regulate a movement of the guide plate 19 relative to the both nip rolls 5 in a direction orthogonal to the travel path E1. Note that denoted by 31 in FIG. 4 are guide rollers for supporting the timing belt 25 from an outer side of the annular path T1.

The timing belt 25, the both timing pulleys 26 and the regulating mechanism (slider 29 and rail 30) are provided on a facing surface 11*b* of the base plate 11 facing the both nip rolls 5. On the other hand, as shown in FIG. 6, the motor 28 includes a main body portion 28*a* arranged on a side of the base plate 11 opposite to the facing surface 11*b* and a rotary shaft 28*b* projecting from the main body portion 28*a*, penetrating through the base plate 11 and connected to the timing pulley 26.

Further, the base plate 11 is formed with a through hole 11*a* penetrating the base plate 11 in the Z direction, and the elastic members EL are supplied to the both nip rolls 5 through this through hole 11*a*. The travel path E1 of the guide plate 19 is arranged at a position overlapping with the through hole 11*a* in the Z direction.

Figure 5A:
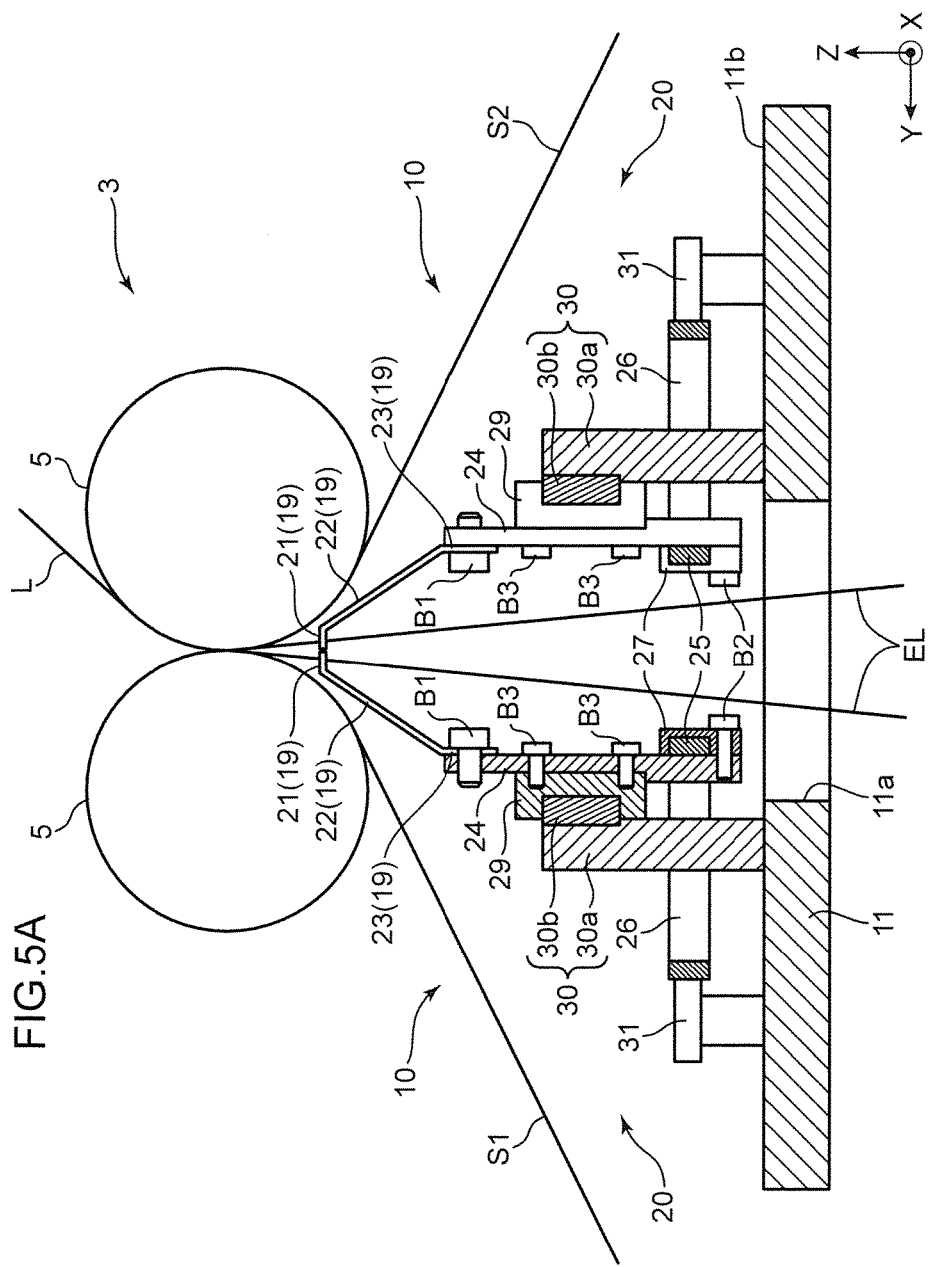
FIG. 5A is a sectional view along line V-V of FIG. 4.

Specifically, as shown in FIGS. 4 and 5A, the both timing pulleys 26 are arranged side by side in the X direction, and a part of one timing pulley 26 is arranged to overlap with the through hole 11*a* in the Z direction. In this way, the annular path T1 arranged to extend in the X direction and partly overlapping with the through hole 11*a* in the Z direction is defined between the both timing pulleys 26. The travel path E1 is set in a range of this annular path T1 overlapping with the through hole 11*a*.

The guide plate 19 and the timing belt 25 are attached to the attached member 24. Specifically, the guide plate 19 is attached to the attached member 24 by a bolt B1 inserted into an insertion hole 23*a* (see FIG. 8) formed on the attaching portion 23 thereof. The timing belt 25 is attached to the attached member 24 by fixing a covering member 27 for covering the timing belt 25 from the outer side of the annular path T1 to the attached member 24 by a bolt B2.

The regulating mechanism includes the slider 29 fixed to the attached member 24 and the rail 30 engaged with the slider 29 in a state where the slider 29 is slidable along the travel path E1, but non-slidable in a direction orthogonal to the travel path E1.

The slider 29 and the rail 30 are respectively provided in a range inside the annular path T1. Further, as shown in FIG. 5B, the slider 29 and the rail 30 are engaged with each other with a gap G defined therebetween in the Y direction orthogonal to the travel path E on a plane including the annular path T1 in a state where no tension is applied to the timing belt 25. Note that the gap G is shown in an exaggerated manner for the sake of description in FIG. 5B.

On the other hand, the slider 29 and the rail 30 are so fixed to each other that tension applied to the timing belt 25 acts in a direction to narrow the gap G. Specifically, the slider 29 is fixed to a surface of the attached member 24 opposite to the timing belt 25 by a bolt B3. Thus, the tension applied to the timing belt 25 acts as a force for pressing the slider 29 toward the rail 30 in the Y direction through the attached member 24. In this way, the gap G in the Y direction between the slider 29 and the rail 30 can be narrowed as shown in FIG. 5A.

Further, the attached positions of the guide plate 19, the timing belt 25 and the slider 29 to the attached member 24 differ in a direction orthogonal to the plane including the annular path T1 (X-Y plane) as shown in FIGS. 4 and 5A. In this way, an area of the X-Y plane occupied by the drive mechanism 20 can be reduced.

The rail 30 includes a support column 30a standing on the facing surface 11b of the base plate 11 and a rail main body 30b fixed to an upper end part of the support column 30a and engaged with the slider 29.

Since a movement of the guide plate 19 in the direction orthogonal to the travel path E1 can be regulated by the regulating mechanism (slider 29 and rail 30) according to the above drive mechanism 20, a variation of the position of the guide plate 19 with respect to the both nip rolls 5 can be suppressed.

Accordingly, the elastic members EL can be stably positioned with respect to the both sheets S1, S2.

Further, the slider 29 and the rail 30 can be arranged utilizing a dead space inside the annular path T1 along which the timing belt 25 is arranged. Thus, it is possible to realize stable positioning of the elastic members EL with respect to the both sheets S1, S2 while suppressing the enlargement of the manufacturing device 1.

The gap (slack) G is provided in the Y direction between the slider 29 and the rail 30 as shown in FIG. 5B to avoid a trouble that the slider 29 and the rail 30 are meshed with each other and cannot be displaced relative to each other.

However, this slack causes the degradation of accuracy in positioning the elastic members EL in a state where the slider 29 and the rail are properly moving.

Accordingly, in the drive mechanism 20, the gap G between the slider 29 and the rail 30 can be narrowed utilizing the tension of the timing belt 25 as shown in FIG. 5A. Thus, the positioning accuracy of the elastic members EL can be further improved.

Further, since the flexible timing belt 25 is used, it is also possible to achieve a desired object of suppressing the mesh of the slider 29 and the rail 30 by providing the gap G therebetween by the deflection of the timing belt 25.

As described above, a variation of the guide plate 19 with respect to the both nip rolls 5 can be suppressed since a movement of the guide plate 19 (guide member) in the direction orthogonal to the travel path E1 can be regulated by the slider 29 and the rail 30 (regulating mechanism).

Thus, the elastic members EL can be stably positioned with respect to the both sheets S1, S2.

Further, according to the above embodiment, the following effects can be exhibited.

Since the slider 29 and/or the rail 30 can be arranged utilizing the dead space inside the annular path T1 along which the timing belt 25 is arranged, it is possible to realize stable positioning of the elastic members EL with respect to the both sheets S1, S2 while suppressing the enlargement of the manufacturing device 1.

Here, the gap (slack) G is provided between the slider 29 and the rail 30 as shown in FIG. 5B to avoid a trouble that the slider 29 and the rail 30 are meshed with each other and cannot be displaced relative to each other when an external force acting in a direction other than that of the travel path E1 set in advance is applied to the slider 29.

However, this slack causes the degradation of accuracy in positioning the elastic members EL in the state where the slider 29 and the rail 30 are properly moving (moving along the travel path E1).

Since the gap G between the slider 29 and the rail 30 can be narrowed utilizing the tension applied to the timing belt 25 as shown in FIG. 5A in the above embodiment, the positioning accuracy of the elastic members EL can be further improved.

Further, since the flexible timing belt 25 is used in the above embodiment, it is also possible to achieve the desired object of suppressing the mesh of the slider 29 and the rail 30 by providing the gap G therebetween by the deflection of the timing belt 25.

Furthermore, since the attached positions of the guide plate 19, the timing belt 25 and the slider 29 to the attached member 24 are respectively different in the direction orthogonal to the plane including the annular path T1 (X-Y plane), the enlargement of the manufacturing device 1 along the X-Y plane can be suppressed.

Further, since the guiding unit 3 and the sandwiching unit 2 can be arranged at positions different from each other in the direction of the axes 5a of the both nip rolls 5 (X direction), maintenance can be performed for the guiding unit 3 and/or the sandwiching unit 2 with one of the guiding unit 3 and the sandwiching unit 2 avoided from the other.

Here, the tip part (holding portion 21) of the guide plate (guide member) 19 may be arranged between the outer circumferential surfaces of the both nip rolls 5 to accurately position the elastic members EL with respect to the both sheets S1, S2.

Even in such a case, since the relative displacement direction of the guiding unit 3 and the sandwiching unit 2 is set in the X direction, it is possible to realize relative displacements of the guide plate 19 and the both nip rolls 5 while avoiding the contact of the holding portion 21 of the guide plate 19 with the both nip rolls 5.

Further, since the sandwiching unit 2 and the guiding unit 3 are supported on the one side in the X direction by the main frame 14, the space opposite to the main frame 14 in the manufacturing device 1 can be utilized as the space for pulling out the guiding unit 3.

With the guiding unit 3 pulled out, the space opposite to the main frame 14 in the manufacturing device 1 can be utilized as the space for the maintenance of the guiding unit 3.

Further, with the guiding unit 3 pulled out to the space opposite to the main frame 14, the sandwiching unit 2 is accessible through the space between the guiding unit holding beams 16.

Accordingly, the operability of maintenance not only for the guiding unit 3, but also for the sandwiching unit 2 can be improved.

Since the lock members 18 are provided in the above embodiment, the movement of the guide plate 3 can be regulated in a situation where the maintenance operation of the manufacturing device 1 is not performed.

Further, at least part of the facing surface 11b of the base plate 11 is opeded from the sandwiching unit 2 by relatively displacing the guiding unit 3 and the sandwiching unit 2, whereby maintenance can be easily performed for the timing belt 25 and the timing pulleys 26 provided on the facing surface 11b.

Since the slider 29 and the rail 30 (regulating mechanism) are provided on the facing surface 11b in the above embodiment, maintenance can be easily performed also for the slider 29 and the rail 30 provided on the facing surface 11b by relatively displacing the guiding unit 3 and the sandwiching unit 2.

A method for manufacturing the elastic laminate L using the aforementioned manufacturing device 1 is described below with reference to FIGS. 1 to 4.

This manufacturing method includes a conveying step, a guiding step and a driving step.

In the conveying step, the pair of sheets S1, S2 are conveyed in the longitudinal directions thereof to be guided to between the pair of nip rolls 5.

In the guiding step, the elastic members EL are guided to between the both sheets S1, S2 while being fed in the longitudinal directions thereof using the guide plates 19 so that the elastic members EL are sandwiched between the both sheets S1, S2 by the pair of nip rolls 5.

In the driving step, the guide plates 19 are driven using the drive mechanisms 20 such that the guide plates 19 reciprocate along the travel paths E1 along the direction of the axes of the both nip rolls 5 (X direction).

Further, in the driving step, movements of the guide plates 19 relative to the both nip rolls 5 along the travel paths E1 are permitted and movements thereof relative to the both nip rolls 5 in the directions orthogonal to the travel paths E1 are regulated using the regulating mechanisms (sliders 29 and the rails 30).

Note that the specific embodiment described above mainly includes inventions having the following configurations.

To solve the above problem, the present invention provides a device for manufacturing an elastic laminate in which an elastic member is sandwiched between a pair of sheets and includes a pair of nip rolls configured to sandwich the pair of sheets with the elastic member interposed between the both sheets conveyed in longitudinal directions of the sheets and arranged such that axes of the pair of nip rolls are parallel, a guide member provided upstream of the both nip rolls in the conveying directions of the both sheets and configured to guide the elastic member to between the both sheets while feeding the elastic member in a longitudinal direction of the elastic member, and a drive mechanism configured to drive the guide member such that the guide member reciprocates along a travel path along a direction of the axes of the both nip rolls. The drive mechanism includes a belt having the guide member fixed thereto, a plurality of pulleys configured such that the belt is provided thereon along an annular path including the travel path, a motor configured to drive the pulleys to be successively rotated in forward and reverse directions to reciprocate the guide member along the travel path and a regulating mechanism configured to permit a movement of the guide member relative to the both nip rolls along the travel path and regulate a movement of the guide member relative to the both nip rolls in a direction orthogonal to the travel path.

According to the present invention, a variation of the position of the guide member with respect to the both nip rolls can be suppressed since the movement of the guide member in the direction orthogonal to the travel path can be regulated by the regulating mechanism.

Thus, according to the present invention, the elastic member can be stably positioned with respect to the both sheets.

In the manufacturing device for the elastic laminate, the regulating mechanism preferably includes a slider fixed to the guide member and a rail engaged with the slider in a state where the slider is slidable along the travel path, but non-slidable in the direction orthogonal to the travel path.

According to the above aspect, the movement of the guide member in the direction orthogonal to the travel path can be regulated by the engagement of the slider and the rail.

In the manufacturing device for the elastic laminate, the rail is preferably provided within a range inside the annular path.

Further, in the manufacturing device for the elastic laminate, the slider is preferably provided within the range inside the annular path.

According to the above aspects, the rail and/or the slider can be arranged utilizing a dead space inside the annular path along which the belt is arranged. Thus, it is possible to realize stable positioning of the elastic member with respect to the both sheets while suppressing the enlargement of the manufacturing device.

Here, a gap (slack) is provided between the slider and the rail to avoid a trouble that the slider and the rail are meshed with each other and cannot be displaced relative to each other when an external force acting in a direction other than a direction of the travel path set in advance is applied to the slider.

However, this slack causes the degradation of accuracy in positioning the elastic member in a state where the slider and the rail are properly moving (moving along the travel path).

Accordingly, in the manufacturing device for the elastic laminate, the slider and the rail are preferably engaged with each other with a gap defined therebetween in a direction orthogonal to the travel path on a plane including the annular path, and the belt is preferably fixed to the slider such that a tension applied to the belt acts to narrow the gap.

According to the above aspect, the positioning accuracy of the elastic member can be further improved since the gap between the slider and the rail can be narrowed utilizing the tension applied to the belt.

Further, since the flexible belt is used in the above aspect, it is possible to achieve also a desired object of suppressing the mesh of the slider and the rail by providing the gap between the slider and the rail by the deflection of the belt.

In the manufacturing device for the elastic laminate, preferably, the drive mechanism further includes an attached member to which the guide member, the belt and the slider are attached such that the attached member is interposed between the guide member, and the belt and the slider and attached positions of the guide member, the belt and the slider with respect to the attached member are respectively different in a direction orthogonal to a plane including the annular path.

According to the above aspect, the enlargement of the manufacturing device along the plane including the annular path can be suppressed as compared to the case where the attached positions of the guide member, the belt and the slider are set on the plane including the annular path.

In the device described in patent literature 1, the guide plate is used as the guide member.

Specifically, the guide plate includes a holding portion arranged in a direction orthogonal to a tangent to the outer circumferential surfaces of both nip rolls at a sandwiching position of the both sheets between the outer circumferential surfaces of the both nip rolls and a part extending from an end part of the holding portion close to one nip roll in a direction to avoid the one nip roll (part bent with respect to the holding portion).

The holding portion is formed with an insertion hole penetrating in a thickness direction thereof and the elastic member is inserted through the insertion hole. This enables the guide plate to feedably hold the elastic member also during the movement thereof.

By the movement of the guide plate, the elastic member can be sandwiched between the both sheets while the position of the elastic member is changed along the axial direction of the both nip rolls.

Here, the holding position of the elastic member by the holding portion needs to be brought closer to the sandwiching position of the both nip rolls to accurately position the elastic member with respect to the both sheets. To that end, the holding portion needs to be formed short.

Further, during the movement of the guide plate along the axial direction, the elastic member is fed in the longitudinal direction thereof while being held in contact with the circumferential surface of the insertion hole. Thus, the elastic member receives a force corresponding to sliding resistance thereof from the holding portion.

Thus, if the holding portion is formed short, a distance (radius) from the bent part to the insertion hole in the guide plate becomes shorter and a bending angle of the holding portion is difficult to change when the holding portion receives a force from the elastic member.

As a result, sliding resistance received by the elastic member may increase and the elastic member may be fractured as compared to the case where the holding portion is formed relatively long.

Accordingly, preferably, the manufacturing device for the elastic laminate includes a guide plate as the guide member, the drive mechanism is provided on the side of one of the both nip rolls with respect to a plane including a tangent to the outer circumferential surfaces of the both nip rolls at a sandwiching position of the both sheets between the outer circumferential surfaces of the both nip rolls, the guide plate includes a holding portion arranged in a direction orthogonal to the tangent and a main body portion extending from an end part of the holding portion closer to the one nip roll in a direction to avoid the one nip roll and attached to the drive mechanism, the holding portion is formed with an insertion hole penetrating through the holding portion in a thickness direction of the holding portion for the passage of the elastic member and a hold-side bent portion between the holding portion and the main body portion in the guide plate is formed with a hold-side hollow portion penetrating through the guide plate in the thickness direction of the guide plate such that a cross-sectional area of the hold-side bent portion is smaller than those of parts of the holding portion and the main body portion adjacent to the hold-side bent portion.

According to the above aspect, the guide plate can be bent at a position closer to a tip side since the cross-sectional area of the hold-side bent portion is made smaller than those of the parts adjacent to the hold-side bent portion by the hold-side hollow portion. Thus, a small holding portion corresponding to the position of the hold-side hollow portion can be realized.

Accordingly, a holding position of the elastic member by the holding portion can be brought closer to the sandwiching position of the both nip rolls, whereby the positioning accuracy of the elastic member with respect to the both sheets can be improved.

In addition, according to the above aspect, the hold-side bent portion is easily elastically deformed as compared to the case where the hold-side bent portion is not provided since the cross-sectional area of the hold-side bent portion is smaller than those of the parts adjacent to the hold-side bent portion.

Thus, when a force received by the holding portion from the elastic member is large, the fracture of the elastic member can be suppressed by reducing sliding resistance against the elastic member by the elasticity of the hold-side bent portion.

Moreover, according to the above aspect, rigidity and power required for the drive mechanism can be reduced since a weight reduction of the guide plate can be realized by the hold-side hollow portion penetrating through the guide plate.

Note that "the holding portion arranged in the direction orthogonal to the tangent to the outer circumferential surfaces of the both nip rolls" in the above aspect means to include also a holding portion inclined with respect to the tangent within a range not to apply a tension more than necessary to the elastic member.

Only one guide plate may be provided, but a plurality of the guide plates may also be provided.

In the case of providing a plurality of guide plates, one drive mechanism can drive only one guide plate and other guide plate(s) can be driven by other driving mechanism(s). Specifically, the manufacturing device for the elastic laminate may include two drive mechanisms provided on the sides of the respective nip rolls with respect to the plane including the tangent and two guide plates attached to the respective drive mechanisms.

Specifically, the hold-side hollow portion can be configured by a hold-side through hole formed between side surfaces of the guide plate and/or a cut formed by recessing a side surface of the guide plate.

In the manufacturing device for the elastic laminate, preferably, a width of the holding portion in the direction of the axes is larger than a width of a part of the main body portion adjacent to the hold-side bent portion and the holding portion is formed with a plurality of the insertion holes arranged side by side in the direction of the axes.

According to the above aspect, the elastic laminate can be formed with a plurality of elastic members sandwiched in parallel to each other since a plurality of elastic members arranged side by side in the direction of the axes can be simultaneously guided to between the both sheets.

Here, if the width of the holding portion is simply made larger to form the plurality of insertion holes in a width direction on the holding portion, the hold-side bent portion is difficult to elastically deform.

However, the guiding of the plurality of elastic members and easy elastic deformation of the hold-side bent portion can be accomplished since the cross-sectional area of the hold-side bent portion is made smaller than those of the parts of the holding portion adjacent to the hold-side bent portion by the hold-side hollow portion.

In the manufacturing device for the elastic laminate, preferably, the main body portion of the guide plate includes a lead-out portion extending from the holding portion to an outer position outwardly of a part sandwiched between the outer circumferential surfaces of the both nip rolls and an attaching portion bent with respect to the lead-out portion at the outer position and attached to the drive mechanism, a maximum width of the attaching portion in the direction of the axes is larger than a maximum width of the lead-out portion, and an attach-side bent portion between the lead-out portion and the attaching portion in the guide plate is formed with a attach-side hollow portion penetrating through the guide plate in the thickness direction of the guide plate so that a cross-sectional area of the attach-side bent portion is smaller than that a part of the attaching portion adjacent to the attach-side bent portion.

According to the above aspect, the guide plate (attaching portion) can be reliably attached to the drive mechanism utilizing a wide area of the attaching portion since the maximum width of the attaching portion is set larger than the maximum width of the lead-out portion.

Here, if the maximum width of the attaching portion is simply made larger than the maximum width of the lead-out portion to ensure a wide area of the attaching portion, the attach-side bent portion is difficult to elastically deform.

However, reliable mounting of the attaching portion and the drive mechanism and easy elastic deformation of the attach-side bent portion can be accomplished since the cross-sectional area of the attach-side bent portion is made smaller than the cross-sectional area of the part of the attaching portion adjacent to the attach-side bent portion by the attach-side hollow portion in the above aspect.

Thus, the fracture of the elastic member can be suppressed by reducing sliding resistance of the elastic member also by the elasticity of the attach-side bent portion according to a force received by the holding portion from the elastic member.

Further, according to the above aspect, a further weight reduction of the guide plate can be realized by the attach-side hollow portion penetrating through the guide plate.

In the manufacturing device for the elastic laminate, preferably, the lead-out portion includes a wide portion adjacent to the attaching portion and gradually widened toward the attaching portion, the attach-side hollow portion includes an attach-side through hole penetrating through the wide portion in a thickness direction of the wide portion, the attach-side through hole has a triangular planar shape having a pair of oblique sides parallel to opposite side surfaces of the wide portion and a bottom side coupling the pair of oblique sides and constituting an end surface of the attaching portion, and the triangular shape is rounded on corner parts.

According to the above aspect, it is possible to suppress an increase in a cross-sectional area of the wide portion by the attach-side through hole and realize a weight reduction while gradually increasing a width of the wide portion toward the attaching portion.

A sufficient area of the attaching portion can be ensured since the bottom side of the attach-side through hole constitutes the end surface of the attaching portion.

As described above, the holding position of the elastic member by the guide member needs to be brought closer to the sandwiching position of the both nip rolls to accurately position the elastic member with respect to the both sheets.

Further, the guide member and the drive mechanism are coupled to each other.

Thus, in the case of performing maintenance for the manufacturing device described in patent literature 1, maintenance needs to be performed in a narrow space where the both nip rolls, the guide member and the drive mechanism are densely arranged. Thus, there is a problem of poor operability.

Accordingly, the manufacturing device for the elastic laminate preferably includes a sandwiching unit including the pair of nip rolls, a guiding unit including the guide member and the drive mechanism and a supporting unit configured to support the sandwiching unit and the guiding unit such that the sandwiching unit and the guiding unit are relatively displaceable along the direction of the axes of the both nip rolls.

According to this aspect, maintenance can be performed for the guiding unit and/or the sandwiching unit with one of the guiding unit and the sandwiching unit avoided from the other since the guiding unit and the sandwiching unit can be arranged at positions different from each other in the direction of the axes of the both nip rolls.

Here, a tip part (part for holding the elastic member) of the guide member may be arranged between the outer circumferential surfaces of the both nip rolls to accurately position the elastic member with respect to the both sheets.

Even in such a case, since a relative displacement direction of the guiding unit and the sandwiching unit is set in the direction of the axes of the both nip rolls in the above aspect, it is possible to realize relative displacements of the guide member and the both nip rolls while avoiding the contact of the tip part of the guide member with the both nip rolls.

In the manufacturing device for the elastic laminate, the supporting unit preferably includes a main frame provided on one side in the direction of the axes with respect to the sandwiching unit and the guiding unit, a sandwiching unit holding mechanism extending along the direction of the axes from the main frame and configured to hold the sandwiching unit and a guiding unit holding mechanism extending along the direction of the axes from the main frame and configured to hold the guiding unit such that the guiding unit is movable along the direction of the axes.

According to the above aspect, a space on a side opposite to the main frame in the manufacturing device can be utilized as a space for pulling out the guiding unit since the sandwiching unit and the guiding unit are supported on the one side in the direction of the axes by the main frame.

With the guiding unit pulled out, the space on the side opposite to the main frame in the manufacturing device can be utilized as a space for the maintenance of the guiding unit.

In the manufacturing device for the elastic laminate, preferably, the guiding unit holding mechanism includes a pair of guiding unit holding beams arranged at a distance from each other in a direction orthogonal to the axes and extending along the direction of the axes from the main frame, and the pair of guiding unit holding beams hold the guiding unit such that the guiding unit is movable along the direction of the axes between the pair of guiding unit holding beams.

According to the above aspect, the sandwiching unit is accessible through a space between the both guiding unit holding beams with the guiding unit pulled out to the space on the side opposite to the main frame.

Thus, the operability of maintenance not only for the guiding unit, but also for the sandwiching unit can be improved.

In the manufacturing device for the elastic laminate, the guiding unit holding mechanism preferably further includes a lock member switchable between a regulating state for regulating a movement of the guiding unit relative to the pair of guiding unit holding beams and a permitting state for permitting the movement of the guiding unit relative to the pair of guiding unit holding beams.

According to the above aspect, the movement of the guiding unit can be regulated in a situation where the maintenance operation of the manufacturing device is not performed.

In the manufacturing device for the elastic laminate, preferably, the guiding unit further includes a base plate having a facing surface facing the pair of nip rolls at a position upstream of the conveying directions of the sheets, and the belt and the plurality of pulleys are provided on the facing surface of the base plate.

According to the above aspect, at least part of the facing surface of the base plate is opened from the sandwiching unit by relatively displacing the guiding unit and the sandwiching unit, whereby maintenance can be easily performed for the belt and the plurality of pulleys provided on the facing surface.

In the manufacturing device for the elastic laminate, the regulating mechanism is preferably provided on the facing surface of the base plate.

According to the above aspect, maintenance can be easily performed also for the regulating mechanism provided on the facing surface by relatively displacing the guiding unit and the sandwiching unit.

Further, the present invention provides a method for manufacturing an elastic laminate using the above manufacturing device and includes a conveying step of conveying the pair of sheets in the longitudinal directions of the pair of sheets such that the sheets are guided to between the pair of nip rolls, a guiding step of guiding the elastic member to between the both sheets while feeding the elastic member in the longitudinal direction of the elastic member using the guide member such that the elastic member is sandwiched between the both sheets by the pair of nip rolls and a driving step of driving the guide member using the drive mechanism such that the guide member reciprocates along a travel path along a direction of axes of the both nip rolls. In the driving step, a movement of the guide member relative to the both nip rolls along the travel path is permitted and a movement of the guide member relative to the both nip rolls in a direction orthogonal to the travel path is regulated using the regulating mechanism.

According to the present invention, a variation of the position of the guide member with respect to the both nip rolls can be suppressed since the movement of the guide member in the direction orthogonal to the travel path can be regulated by the regulating mechanism.

Thus, according to the present invention, the elastic member can be stably positioned with respect to the both sheets.

The invention claimed is:
1. A device for manufacturing an elastic laminate in which an elastic member is sandwiched between a pair of sheets, comprising:
   a pair of nip rolls configured to sandwich the pair of sheets with the elastic member interposed between the both sheets conveyed in longitudinal directions of the sheets and arranged such that axes of the pair of nip rolls are parallel;
   a guide member provided upstream of the both nip rolls in the conveying directions of the both sheets and configured to guide the elastic member to between the both sheets while feeding the elastic member in a longitudinal direction of the elastic member; and
   a drive mechanism configured to drive the guide member such that the guide member reciprocates along a travel path along a direction of the axes of the both nip rolls,
   the drive mechanism including a belt having the guide member fixed thereto, a plurality of pulleys configured such that the belt is provided thereon along an annular path including the travel path, a motor configured to drive the pulleys to be successively rotated in forward and reverse directions to reciprocate the guide member along the travel path and a regulating mechanism configured to permit a movement of the guide member relative to the both nip rolls along the travel path and regulate a movement of the guide member relative to the both nip rolls in a direction orthogonal to the travel path, the regulating mechanism includes a slider fixed to the guide member and a rail engaged with the slider in a state where the slider is slidable along the travel path, but non-slidable in the direction orthogonal to the travel path, the slider being provided within a range inside the annular path, wherein:
   the slider and the rail are engaged with each other with a gap defined therebetween in a direction orthogonal to the travel path on a plane including the annular path; and
   the belt is fixed to the slider such that a tension applied to the belt acts to narrow the gap.

2. A device for manufacturing an elastic laminate according to claim 1, wherein:
   the drive mechanism further includes an attached member to which the guide member, the belt and the slider are attached such that the attached member is interposed between the guide member, and the belt and the slider; and
   attached positions of the guide member, the belt and the slider with respect to the attached member are respectively different in a direction orthogonal to a plane including the annular path.

3. A device for manufacturing an elastic laminate according to claim 1, comprising:
   a sandwiching unit including the pair of nip rolls;
   a guiding unit including the guide member and the drive mechanism; and
   a supporting unit configured to support the sandwiching unit and the guiding unit such that the sandwiching unit and the guiding unit are relatively displaceable along the direction of the axes of the both nip rolls.

4. A device for manufacturing an elastic laminate according to claim 3, wherein the supporting unit includes a main frame provided on one side in the direction of the axes with respect to the sandwiching unit and the guiding unit, a sandwiching unit holding mechanism extending along the direction of the axes from the main frame and configured to hold the sandwiching unit and a guiding unit holding mechanism extending along the direction of the axes from the main frame and configured to hold the guiding unit such that the guiding unit is movable along the direction of the axes.

5. A device for manufacturing an elastic laminate according to claim 4, wherein:
   the guiding unit holding mechanism includes a pair of guiding unit holding beams arranged at a distance from each other in a direction orthogonal to the axes and extending along the direction of the axes from the main frame; and
   the pair of guiding unit holding beams hold the guiding unit such that the guiding unit is movable along the direction of the axes between the pair of guiding unit holding beams.

6. A device for manufacturing an elastic laminate according to claim 5, wherein the guiding unit holding mechanism further includes a lock member switchable between a regulating state for regulating a movement of the guiding unit relative to the pair of guiding unit holding beams and a permitting state for permitting the movement of the guiding unit relative to the pair of guiding unit holding beams.

7. A device for manufacturing an elastic laminate according to claim 3, wherein:
the guiding unit further includes a base plate having a facing surface facing the pair of nip rolls at a position upstream of the conveying directions of the sheets; and
the belt and the plurality of pulleys are provided on the facing surface of the base plate.

8. A device for manufacturing an elastic laminate according to claim 7, wherein the regulating mechanism is provided on the facing surface of the base plate.

9. A device for manufacturing an elastic laminate in which an elastic member is sandwiched between a pair of sheets, comprising:
a pair of nip rolls configured to sandwich the pair of sheets with the elastic member interposed between the both sheets conveyed in longitudinal directions of the sheets and arranged such that axes of the pair of nip rolls are parallel;
a guide member comprising a guide plate provided upstream of the both nip rolls in the conveying directions of the both sheets and configured to guide the elastic member to between the both sheets while feeding the elastic member in a longitudinal direction of the elastic member; and
a drive mechanism configured to drive the guide member such that the guide member reciprocates along a travel path along a direction of the axes of the both nip rolls, the drive mechanism being provided on the side of one of the both nip rolls with respect to a plane including a tangent to the outer circumferential surfaces of the both nip rolls at a sandwiching position of the both sheets between the outer circumferential surfaces of the both nip rolls, the drive mechanism including a belt having the guide member fixed thereto, a plurality of pulleys configured such that the belt is provided thereon along an annular path including the travel path, a motor configured to drive the pulleys to be successively rotated in forward and reverse directions to reciprocate the guide member along the travel path and a regulating mechanism configured to permit a movement of the guide member relative to the both nip rolls along the travel path and regulate a movement of the guide member relative to the both nip rolls in a direction orthogonal to the travel path; wherein:
the guide plate includes a holding portion arranged in a direction orthogonal to the tangent and a main body portion extending from an end part of the holding portion closer to the one nip roll in a direction to avoid the one nip roll and attached to the drive mechanism;
the holding portion is formed with an insertion hole penetrating through the holding portion in a thickness direction of the holding portion for the passage of the elastic member; and
a hold-side bent portion between the holding portion and the main body portion in the guide plate is formed with a hold-side hollow portion penetrating through the guide plate in the thickness direction of the guide plate such that a cross-sectional area of the hold-side bent portion is smaller than those of parts of the holding portion and the main body portion adjacent to the hold-side bent portion.

10. A device for manufacturing an elastic laminate according to claim 9, wherein the regulating mechanism includes a slider fixed to the guide member and a rail engaged with the slider in a state where the slider is slidable along the travel path, but non-slidable in the direction orthogonal to the travel path.

11. A device for manufacturing an elastic laminate according to claim 10, wherein the rail is provided within a range inside the annular path.

12. A device for manufacturing an elastic laminate according to claim 11, wherein the slider is provided within the range inside the annular path.

13. A device for manufacturing an elastic laminate according to claim 12, wherein:
the slider and the rail are engaged with each other with a gap defined therebetween in a direction orthogonal to the travel path on a plane including the annular path; and
the belt is fixed to the slider such that a tension applied to the belt acts to narrow the gap.

14. A device for manufacturing an elastic laminate according to claim 9, comprising two drive mechanisms provided on the sides of the respective nip rolls with respect to the plane including the tangent and two guide plates attached to the respective drive mechanisms.

15. A device for manufacturing an elastic laminate according to claim 9, wherein the hold-side hollow portion includes a hold-side through hole formed between side surfaces of the guide plate.

16. A device for manufacturing an elastic laminate according to claim 9, wherein the hold-side hollow portion includes a cut formed by recessing a side surface of the guide plate.

17. A device for manufacturing an elastic laminate according to claim 9, wherein:
a width of the holding portion in the direction of the axes is larger than a width of a part of the main body portion adjacent to the hold-side bent portion; and
the holding portion is formed with a plurality of the insertion holes arranged side by side in the direction of the axes.

18. A device for manufacturing an elastic laminate according to claim 9, wherein:
the main body portion of the guide plate includes a lead-out portion extending from the holding portion to an outer position outwardly of a part sandwiched between the outer circumferential surfaces of the both nip rolls and an attaching portion bent with respect to the lead-out portion at the outer position and attached to the drive mechanism;
a maximum width of the attaching portion in the direction of the axes is larger than a maximum width of the lead-out portion; and
an attach-side bent portion between the lead-out portion and the attaching portion in the guide plate is formed with a attach-side hollow portion penetrating through the guide plate in the thickness direction of the guide plate so that a cross-sectional area of the attach-side bent portion is smaller than that a part of the attaching portion adjacent to the attach-side bent portion.

19. A device for manufacturing an elastic laminate according to claim 18, wherein:
the lead-out portion includes a wide portion adjacent to the attaching portion and gradually widened toward the attaching portion;

the attach-side hollow portion includes an attach-side through hole penetrating through the wide portion in a thickness direction of the wide portion; and the attach-side through hole has a triangular planar shape having a pair of oblique sides parallel to opposite side surfaces of the wide portion and a bottom side coupling the pair of oblique sides and constituting an end surface of the attaching portion.

* * * * *